(12) United States Patent
Goldberg et al.

(10) Patent No.: US 8,114,593 B2
(45) Date of Patent: Feb. 14, 2012

(54) CANCER BIOMARKER GENES AND GENE PRODUCTS AND METHODS FOR USING THE SAME

(75) Inventors: Gary S. Goldberg, Voorhees, NJ (US); Yongquan Shen, Voorhees, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 113 days.

(21) Appl. No.: 12/401,849

(22) Filed: Mar. 11, 2009

(65) Prior Publication Data

US 2009/0232814 A1    Sep. 17, 2009

Related U.S. Application Data

(60) Provisional application No. 61/085,039, filed on Jul. 31, 2008, provisional application No. 61/069,198, filed on Mar. 12, 2008.

(51) Int. Cl.
*C12Q 1/68* (2006.01)
*G01N 33/53* (2006.01)
*G01N 33/567* (2006.01)
*G01N 33/566* (2006.01)
*G01N 33/574* (2006.01)
*C07K 16/18* (2006.01)
*C07K 16/28* (2006.01)
*C07K 16/30* (2006.01)

(52) U.S. Cl. ...... 435/6.1; 435/6.13; 435/6.14; 435/6.17; 435/6.19; 435/7.1; 435/7.2; 435/7.21; 435/7.23; 436/63; 436/64; 436/501; 530/387.1

(58) Field of Classification Search ............. None
See application file for complete search history.

(56) References Cited

U.S. PATENT DOCUMENTS

2008/0176240 A1 *  7/2008  St. Jean .................. 435/6

FOREIGN PATENT DOCUMENTS

WO     WO2007/103541     *  9/2008

OTHER PUBLICATIONS

PubMed synonyms for TMEM163 (downloaded frm the Web on a/12/11).*
Burre et al (Journal of Neurochemistry, Nov. 2007, vol. 103, pp. 276-287).*
Sugimoto et al (Cancer Research, 1991, vol. 51, pp. 921-925).*
Kato et al (BBRC, 2006, vol. 349, pp. 1301-1307).*
Suzuki-Inoue et al (Journal of Biological Chemistry, 2007, vol. 282, pp. 25993-26001).*
Burnham et al., "The identification of p130$^{cas}$-binding proteins and their role in cellular transformation", Oncogene 1996 12:2467-2472.
Sakai et al., "A novel signaling molecule, p130, forms stable complexes in vivo with v-Crk and v-Src in a tyrosine phosphorylation-dependent manner", EMBO J. 1994 13(16):3748-3756.
Schlaepfer et al., "Signaling through focal adhesion kinase", Progress in Biophysics & Molecular Biology 1999 71:435-478.
Shen et al., Src uses Cas to suppress Fhl1 in order to promote nonanchored growth and migration of tumor cells, Cancer Research 2006 66(3):1543-1552.
Sieg et al., "Required role of focal adhesion kinase (FAK) for integrin-stimulated cell migration", Journal of Cell Science 1999 112:2677-2691.
Vuori et al., "Induction of p130$^{cas}$ signaling complex formation upon integrin-mediated cell adhesion:a role for Src family kinases", Molecular and Cellular Biology 1996 16(6):2606-2613.

* cited by examiner

*Primary Examiner* — Karen Canella
(74) *Attorney, Agent, or Firm* — Licata & Tyrrell P.C.

(57) ABSTRACT

Using gene expression analysis, specific biomarker genes and gene products have been identified which are activated in transformed cells, but suppressed in nontransformed cells; or suppressed in transformed cells, but activated in transformed cells affected by Contact Normalization. Thus, the present invention features compositions and methods for detecting, diagnosing, treating and prognosing cancer.

9 Claims, 1 Drawing Sheet

CANCER BIOMARKER GENES AND GENE PRODUCTS AND METHODS FOR USING THE SAME

This application claims benefit of priority from U.S. Provisional Patent Application Ser. Nos. 61/069,198, filed Mar. 12, 2008, and 61/085,039, filed Jul. 31, 2008, the content of which is incorporated herein by reference in its entirety.

This invention was made with government support under grant number CA88805-01A2 awarded by the National Institutes of Health. The government has certain rights in the invention.

BACKGROUND OF THE INVENTION

Progress in methods to detect and treat cancer has led to increased five-year survival rates. However, cancer mortality rates have not decreased proportionately (Welch, et al. (2000) *JAMA* 283:2975-2978). Some transformed cells can survive medical treatment and lay dormant for years before they emerge to cause relapse in a patient. Nontransformed cells can force tumor cells to assume a normal morphology and phenotype by a process called "Contact Normalization" (Glick & Yuspa (2005) *Semin. Cancer Biol.* 15:75-83; Rubin (2003) *Adv. Cancer Res.* 90:1-62).

Increased anchorage-independent growth and migration distinguish cancer cells from their nontransformed precursors (Frisch & Screaton (2001) *Curr. Opin. Cell Biol.* 13:555-562; Giancotti & Buoslahti (1999) *Science* 285:1028-1032). Src kinase, a membrane-bound tyrosine kinase, phosphorylates Cas (Crk associated substrate) to promote these fundamental hallmarks of tumor cell growth (Brabek, et al. (2004) *Oncogene* 23:7406-7415; Cho & Klemke (2000) *J. Cell Biol.* 149: 223-236; Goldberg, et al. (2003) *J. Biol. Chem.* 278:46533-46540; Honda, et al. (1998) *Nat. Genet.* 19:361-365; Huang, et al. (2002) *J. Biol. Chem.* 277:27265-27272; Klemke, et al. (1998) *J. Cell Biol.* 140:961-972; Shin, et al. (2004) *J. Biol. Chem.* 279:38331-38337).

Src has been implicated in many human cancers (Frame (2002) *Biochim. Biophys. Acta* 1602:114-130; Irby & Yeatman (2000) *Oncogene* 19:5636-5642). Increased Src activity has been reported in cancers of the colon (Cartwright, et al. (1994) *J. Clin. Invest* 93:509-515; Cartwright, et al. (1989) *J. Clin. Invest* 83:2025-2033; Cartwright, et al. (1990) *Proc. Natl. Acad. Sci. USA* 87:558-562), and particularly in metastatic colon cancer that invades liver (Termuhlen, et al. (1993) *J. Surg. Res.* 54:293-298). Increased Src activity is also found in cancers of the pancreas (Lutz, et al. (1998) *Biochem. Biophys. Res. Commun.* 243:503-508), lung (Mazurenko, et al. (1992) *Eur. J. Cancer* 28:372-377); neural cells (Bjelfman, et al. (1990) *Mol. Cell. Biol.* 10:361-370; Bolen, et al. (1985) *Proc. Natl. Acad. Sci. USA* 82:7275-7279), muscle (Rosen, et al. (1986) *J. Biol. Chem.* 261:13754-13759), ovaries (Budde, et al. (1994) *Cancer Biochem. Biophys.* 14:171-175; Wiener, et al. (1999) *Clin. Cancer Res.* 5:2164-2170), esophagus (Kumble, et al. (1997) *Gastroenterology* 112:348-356), skin (Bjorge, et al. (1996) *Biochem. Cell Biol.* 74:477-484; Munshi, et al. (2000) *J. Immunol.* 164:1169-1174), stomach (Takeshima, et al. (1991) *Jpn. J. Cancer Res.* 82:1428-1435), and breast (Ottenhoff-Kalff, et al. (1992) *Cancer Res.* 52:4773-4778; Rosen, et al. (1986) supra; Verbeek, et al. (1996) *J. Pathol.* 180:383-388). Indeed, metastatic cell growth can be reduced by agents that inhibit Src activity (Lutz, et al. (1998) supra; Roginskaya, et al. (1999) *Leukemia* 13:855-861; Staley, et al. (1997) *Cell Growth Differ.* 8:269-274).

Cas is an important component of the focal adhesion complex signaling network (Bouton, et al. (2001) *Oncogene* 20:6448-6458) that also includes FAK, Grb2, Shc, and paxillin (Schlaepfer, et al. (1999) *Prog. Biophys. Mol. Biol.* 71:435-478; Sieg, et al. (1999) *J. Cell Sci.* 112 (Pt 16):2677-2691). After phosphorylation by Src, Cas can bind to other proteins including Crk, PI-3-kinase, Nc, and PLCγ (Burnham, et al. (1996) *Oncogene* 12:2467-2472; Sakai, et al. (1994) *EMBO J.* 13:3748-3756; Vuori, et al. (1996) *Mol. Cell. Biol.* 16:2606-2613). Src transformation of homozygous null Cas knockout (CasKO) cells does not fully promote their anchorage-independence or ability to migrate. These transformed growth characteristics can be conferred to CasKO cells by transfection with wild-type Cas (Brabek, et al. (2005) *Mol. Cancer. Res.* 3:307-315; Goldberg, et al. (2003) supra; Honda, et al. (1998) supra; Huang, et al. (2002) supra).

Src phosphosphorylates Cas to inhibit Fhl1 expression thereby promoting nonanchored cell growth and migration (Shen, et al. (2006) *Cancer Res.* 66:1543-1552). Fhl1 is composed of four and half LIM domains and can move between intercellular junctions (Huang, et al. (2002) *Yi. Chuan Xue. Bao.* 29:953-958), focal adhesions, and the nucleus (Brown, et al. (1999) *J. Biol. Chem.* 274:27083-27091) to affect gene expression (Qin, et al. (2005) *FEBS Lett.* 579:1220-1226; Taniguchi, et al. (1998) *Mol. Cell. Biol.* 18:644-654). Transfection studies demonstrate that Fhl1 specifically blocks nonanchored tumor cell growth and migration, but does not affect "normal" anchored cell growth (Shen, et al. (2006) supra). Therefore, Fhl1 acts as a true tumor suppressor rather than as a general mitotic inhibitor. Analysis of human clinical specimens suggests that Fhl1 expression is suppressed in some human tumors including those of breast, kidney, and prostate. Furthermore, Fhl1 expression is suppressed by Src, and is restored during Contact Normalization of transformed cells (Shen, et al. (2006) supra). Thus, Fhl1 acts downstream of Src and Cas to suppress the anchorage-independence and motility that leads to metastatic cell growth.

SUMMARY OF THE INVENTION

The present invention features methods for detecting cells affected by Contact Normalization as wells as methods for diagnosing or prognosing cancer based upon the detection and quantification of selected biomarker gene or gene product which have been correlated with cancer.

A method for identifying a chemotherapeutic agent and kits including binding agents of the invention are also provided.

DETAILED DESCRIPTION OF THE INVENTION

Figure 1:
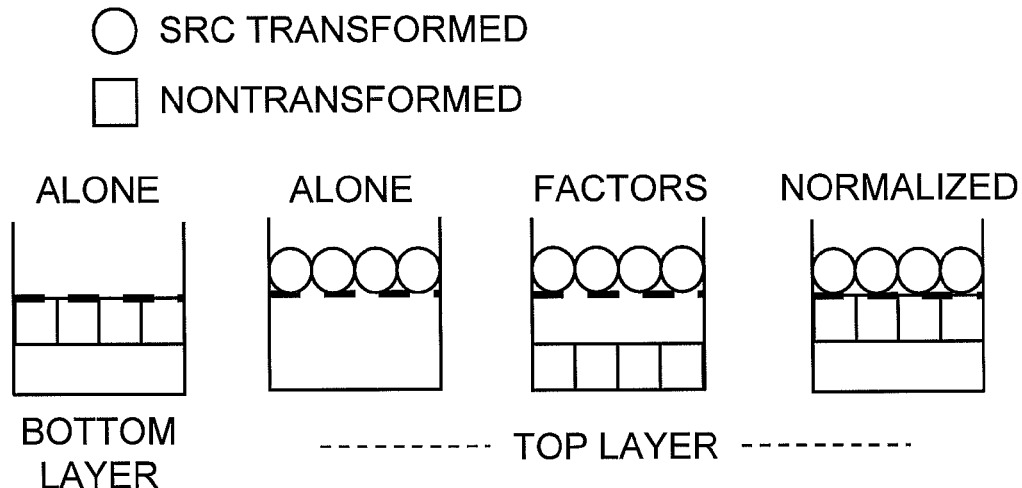
FIG. 1 depicts a layered culture system. Nontransformed or Src transformed Cx43Ko cells were incubated beneath or on top of a porous membrane that prevents actual mixing of the cell populations. Transformed cells separated by 1 mm from nontransformed cells enabled communication by diffusible factors but not intercellular junctions. Transformed cells incubated directly over nontransformed cells allowed for intercellular junctional communication and Contact Normalization.

A comprehensive analysis has now been performed to identify genes that are modulated during Contact Normalization. Contact Normalization describes the ability of nontransformed cells (i.e., normal cells) to normalize the growth of neighboring transformed or cancer cells. Tumor cells need to overcome this form of growth inhibition before they can become malignant or metastatic. The analysis herein identified specific genes which were activated in transformed cells, but suppressed in nontransformed cells. Moreover, the expression of these genes was inhibited in transformed cells that were undergoing Contact Normalization. In addition, genes whose expression was decreased in transformed cells, but increased by Contact Normalization were also identified. Thus, these genes serve as viable biomarkers and chemotherapeutic targets in the diagnosis, prognosis and treatment of cancer. Indeed, the genes and gene products disclosed herein find application as accurate biomarkers to detect cancer; as prognostic indicators to determine the invasive and metastatic potential of cancer cells; surrogate end point markers for drug response, and as chemotherapeutic targets to specifically block malignant cancer cells and neutralize their invasive and metastatic growth potential by application of nontoxic compounds. In so far as these genes are associated with malignant and metastatic cancer, the therapeutic agents targeting these molecules are not expected to interfere with other noncancerous cells in the body.

Accordingly, the present invention features biomarker gene and gene products for detecting and targeting cancer cells, in particular cancer cells affected by Contact Normalization. As is conventional in the art, a biomarker gene or gene product is a gene or gene product that is objectively measured and evaluated as an indicator of a pathogenic process (e.g., cancer), or pharmacologic responses to a therapeutic intervention.

A biomarker gene as used herein refers to a DNA, cDNA, mRNA, and/or coding sequence disclosed herein, the expression of which is increased or decreased in transformed cells (i.e., malignant and metastatic cancer cells) as compared to nontransformed cells; or increased or decreased during Contact Normalization as compared to transformed cells not undergoing Contact Normalization. For use in the methods disclosed herein, it is desirable that the biomarker gene is in isolated form and includes polynucleotides encoding a protein and fragments thereof, DNA, RNA, DNA/RNA hybrid, and related molecules, polynucleotides or oligonucleotides complementary to a nucleic acid disclosed herein or a part thereof, and polynucleotides or oligonucleotides that hybridize or bind to a nucleic acid disclosed herein. As used herein, the disclosed gene and gene products are meant to include the genes and gene products specifically described herein and the genes and gene products which are structurally similar variants of the foregoing. Such other genes and gene products will generally have coding sequences that are highly homologous to the coding sequences disclosed herein, and preferably will share at least about 50% amino acid identity and at least about 60% amino acid identity (using BLAST criteria), more desirably sharing 70%, 80%, 90%, 95% or 99% amino acid sequence identity (using BLAST criteria).

Exemplary biomarker gene (nucleotide) and gene products (proteins) of use in accordance with the present invention are listed in Table 1.

TABLE 1

| Biomarker Symbol | Biomarker Full Name | Nucleotide* | Protein* |
|---|---|---|---|
| 1700012B09Rik | RIKEN cDNA 1700012B09 gene | XM_926406 | XP_931499 |
| Tmem163 | Transmembrane protein 163 | NM_030923 | NP_112185 |
| Smoc2 | SPARC related modular calcium binding 2 | NM_022138 | NP_071421 |
| Pstpip2 | Proline-serine-threonine phosphatase-interacting protein 2 | NM_024430 | NP_077748 |
| Mal | Myelin and lymphocyte protein | NM_002371 | NP_002362 |
| Lepr | Leptin receptor | NM_001003679 NM_001003680 NM_002303 | NP_001003679 NP_001003680 NP_002294 |
| Elavl2 | Embryonic lethal, abnormal vision-like 2 | NM_004432 | NP_004423 |
| Igsf11 | Immunoglobulin superfamily, member 11 | NM_001015887 NM_152538 | NP_001015887 NP_689751 |
| Mafb | v-maf protein B | NM_005461 | NP_005452 |
| LOC677224 | Similar to RIKEN cDNA 2810457I06 | XR_034093 | |
| 4930408O21Rik | RIKEN cDNA 4930408O21 gene | NM_001040136 NM_001040137 | NP_001035226 NP_001035227 |
| Elmod1 | ELMO domain containing 1 | NM_001130037 NM_018712 | NP_001123509 NP_061182 |
| Atp13a4 | ATPase type 13A4 | NM_032279 | NP_115655 |
| Kdr | Kinase insert domain protein receptor | NM_002253 | NP_002244 |

TABLE 1-continued

| Biomarker Symbol | Biomarker Full Name | Nucleotide* | Protein* |
|---|---|---|---|
| C9 | Complement component 9 | NM_001737 | NP_001728 |
| Fgf7 | Fibroblast growth factor 7 | NM_002009 | NP_002000 |
| D10Bwg1379e | DNA segment, Chr 10, Brigham & Women's Genetics 1379 expressed | NM_001033258 | NP_001028430 |
| Sox11 | SRY-box containing gene 11 | NM_003108 | NP_003099 |
| Ccl20 | Chemokine (C-C motif) ligand 20 | NM_001130046<br>NM_004591 | NP_001123518<br>NP_004582 |
| Sema3e | Semaphorin 3E | NM_012431 | NP_036563 |
| Epha4 | EPH receptor A4 | NM_004438 | NP_004429 |
| Ntn1 | Netrin 1 | NM_004822 | NP_004813 |
| Cabc1 | Chaperone, ABC1 activity of bc1 complex homolog (S. pombe) | NM_020247 | NP_064632 |
| Spry1 | Sprouty homolog 1 (Drosophila) | NM_005841<br>NM_199327 | NP_005832<br>NP_955359 |
| Loxl1 | Lysyl oxidase-like 1 | NM_005576 | NP_005567 |
| Pard3b (1810008K04Rik) | Par-3 partitioning defective 3 homolog B | NM_057177<br>NM_152526 | NP_476518<br>NP_689739 |
| Pdgfrb | Platelet-derived growth factor receptor, beta polypeptide | NM_002609 | NP_002600 |
| D4Bwg0951e (LOC286343) | DNA segment, Chr 4, Brigham & Women's Genetics 0951 expressed | NM_203403 | NP_981948 |
| Gpr126 | G protein-coupled receptor 126 | NM_001032394<br>NM_001032395<br>NM_020455<br>NM_198569 | NP_001027566<br>NP_001027567<br>NP_065188<br>NP_940971 |
| Egfr | Epidermal growth factor receptor | NM_005228<br>NM_201282<br>NM_201283<br>NM_201284 | NP_005219<br>NP_958439<br>NP_958440<br>NP_958441 |
| Itih2 | Inter-alpha trypsin inhibitor, heavy chain 2 | NM_002216 | NP_002207 |
| Epb4ll3 | Erythrocyte membrane protein band 4.1-like 3 | NM_012307 | NP_036439 |
| Il1rl1 | Interleukin 1 receptor-like 1 | NM_003856<br>NM_016232 | NP_003847<br>NP_057316 |
| Wnt5a | Wingless-related MMTV integration site 5A | NM_003392 | NP_003383 |
| Tmem56 | Transmembrane protein 56 | NM_152487 | NP_689700 |

*Accession No. available from the National Center for Biotechnology Information Nucleotide and Protein databases.

In particular embodiments, between 1 and 10, 2 and 10, 3 and 10, 4 and 10, 5 and 10, 6 and 10, 7 and 10, 8 and 10, 9 and 10, or 10 of the biomarkers are listed in Table 1 are used in the compositions and methods of this invention. In one embodiment, the biomarker gene or gene product is one or more of 1700012B09Rik, Tmem163, LOC677224, 4930408O21Rik, 1810008K04Rik, and D4Bwg0951e. In another embodiment, the biomarker is one or more of 1700012B09Rik, Tmem163, Pard3b, and D4Bwg0951e.

In other embodiments of the invention, the biomarkers of Table 1 are used in combination with one or more of the gene or gene products listed in Table 2. In accordance with this embodiment, 1, 2, 3, or 4 of the biomarkers listed in Table 2 are used in combination with one or more of the biomarkers listed in Table 1.

TABLE 2

| Biomarker Symbol | Biomarker Full Name | Nucleotide* | Protein* |
|---|---|---|---|
| Pdpn | Podoplanin | NM_001006624<br>NM_001006625<br>NM_006474<br>NM_198389 | NP_001006625<br>NP_001006626<br>NP_006465<br>NP_938203 |
| Vcam1 | Vascular cell adhesion molecule 1 | NM_001078<br>NM_080682 | NP_001069<br>NP_542413 |
| Sdpr | Serum deprivation response | NM_004657 | NP_004648 |
| Fhl1 | Four and a half LIM domains 1 | NM_001449 | NP_00144 |

*Accession No. available from the National Center for Biotechnology Information Nucleotide and Protein databases.

Particular embodiments of the invention disclosed herein include biomarker polynucleotides containing specific portions of the biomarker mRNA sequence (and those which are complementary to such sequences) such as those that encode the biomarker protein and fragments thereof. For example, representative embodiments of the invention disclosed herein include polynucleotides encoding a 10, 20, 30, 40, 50, 60, 70, 80, 90, 100 amino acid residue or full length biomarker protein.

Polynucleotides of the invention have a number of different specific uses. For example, polynucleotides of the invention can be used in the detection, diagnosis or prognosis of cancer, in particular malignant and/or metastatic cancer or cancer cells affected by Contact Normalization. In addition, the polynucleotides of the invention can be used in the design of ribozymes, siRNA or antisense molecules which bind to and inhibit the expression of biomarker genes, e.g., genes whose expression is elevated in transformed cells compared to non-transformed cells or whose expression has been shown to be decreased during Contact Normalization. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets. See for example, Jack Cohen (1988) Oligodeoxynucleotides, Antisense Inhibitors of Gene Expression, CRC Press. Antisense oligonucleotides of the present invention include derivatives such as S-oligonucleotides (phosphorothioate derivatives or S-oligos, see, Jack Cohen, supra), which may exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. S-oligos can be prepared by treatment of the corresponding O-oligos with 3H-1,2-benzodithiol-3-one-1, 1-dioxide, which is a sulfur transfer reagent. See Iyer, et al. (1990) *J. Org. Chem.* 55:4693-4698 and Iyer, et al. (1990) *J. Am. Chem. Soc.* 112:1253-1254. Additional antisense oligonucleotides of the present invention include morpholino antisense oligonucleotides known in the art (see e.g. Partridge, et al. (1996) *Antisense & Nucleic Acid Drug Development* 6:169-175).

Antisense oligonucleotides of the present invention typically can be RNA or DNA that is complementary to and stably hybridizes or binds with a portion of the genomic sequence or the corresponding mRNA. While absolute complementarity is not required, high degrees of complementarity are preferred. Preferably, an antisense oligonucleotide of the present invention is a 15 to 30-mer fragment of the antisense DNA molecule having a sequence that hybridizes to a biomarker mRNA. Alternatively, the antisense molecules are modified to employ ribozymes in the inhibition of biomarker expression (Couture & Stinchcomb (1996) *Trends Genet.* 12: 510-515).

RNAi also allows for the selective knockout of a biomarker gene in a highly effective and specific manner. This technique involves introducing into a cell double-stranded RNA (dsRNA), having a sequence corresponding to the exon portion of the target biomarker gene. The dsRNA causes a rapid destruction of the target gene's mRNA. See, e.g., Hammond, et al. (2001) *Nature Rev. Gen.* 2:110-119; Sharp (2001) *Genes Dev.* 15:485-490. Methods and procedures for successful use of RNAi technology are well-known in the art, and have been described in, for example, Waterhouse, et al. (1998) *Proc. Natl. Acad. Sci. USA* 95(23):13959-13964. A short interfering RNA (siRNA) denotes a small interfering RNA that has a sequence complementary to a sequence within the biomarker gene. Typically, siRNAs are about 20 to 23 nucleotides in length. The target sequence that binds the siRNA can be selected experimentally or empirically. For example, empirical observations have indicated that shRNA oligonucleotides targeting the transcriptional start site of the target gene (Hannon (2002) *Nature* 418:244-51) or targeting the 3' untranslated region of the mRNA (He and Hannon (2004) *Nature* 5:522-531) are more effective at blocking gene expression. Further, siRNA target sites in a gene of interest are selected by identifying an AA dinucleotide sequence, typically in the coding region, and not near the start codon (within 75 bases) as these may be richer in regulatory protein binding sites which can interfere with binding of the siRNA (see, e.g., Elbashir, et al. (2001) *Nature* 411: 494-498). The subsequent 19-27 nucleotides 3' of the AA dinucleotide can be included in the target site and generally have a G/C content of 30-50%.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using *E. coli* RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp, et al. (2002) *Science* 296(5567): 550-3; Lee, et al. (2002) *Nat. Biotechnol.* 20(5):500-5; Miyagashi and Taira (2002) *Nat. Biotechnol.* 20(5):497-500; Paddison, et al. (2002) *Proc. Natl. Acad. Sci. USA* 99(3):1443-8; Paul, et al. (2002); and Sui, et al. (2002) *Proc. Natl. Acad. Sci. USA* 99(8):5515-20. Various methods for introducing such vectors into cells, either in vitro or in vivo (e.g., gene therapy) are known in the art.

Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

Further specific embodiments of this invention include primers and primer pairs, which bind to biomarker genes and allow the specific amplification of the polynucleotides of the invention or of any specific parts thereof, and probes that selectively or specifically bind or hybridize to polynucleotide molecules of the invention or to any part thereof. Probes can be labeled with a detectable biomarker, such as, for example, a radioisotope, fluorescent compound, bioluminescent compound, a chemiluminescent compound, metal chelator or enzyme. Such probes and primers are agents which can be used to detect the presence or quantity of a biomarker polynucleotide in a sample and as a means for detecting a cell expressing a biomarker protein.

Examples of such probes include polynucleotides encompassing all or part (e.g., 10 to 100 nucleotides) of a nucleotide sequence listed in Table 1 or Table 2. As will be understood by the skilled artisan, a great many different primers and probes can be prepared based on the sequences provided herein and used effectively to amplify and/or detect a biomarker mRNA. By way of example, primers of use in this invention are listed in Example 1.

The polynucleotides of the invention are useful for a variety of purposes, including but not limited to their use as probes and primers for the amplification and/or detection of the biomarker gene(s), mRNA(s), or fragments thereof; as reagents for the diagnosis and/or prognosis of cancer; as coding sequences capable of directing the expression of biomarker polypeptides; as tools for modulating or inhibiting the expression of the biomarker gene(s) and/or translation of the biomarker transcript(s); and as therapeutic agents.

The DNA sequences described herein enable the isolation of other polynucleotides encoding biomarker gene product(s), as well as the isolation of polynucleotides encoding biomarker gene product homologs, alternatively spliced isoforms, allelic variants, and mutant forms of the biomarker gene product. Various molecular cloning methods that can be employed to isolate full length cDNAs encoding a biomarker gene are well-known (See, e.g., Sambrook, et al. (1989) Molecular Cloning: A Laboratory Manual, 2d ed., Cold Spring Harbor Press, New York; Ausubel, et al., eds. (1995) Current Protocols in Molecular Biology, Wiley and Sons). For example, lambda phage cloning methodologies can be conveniently employed, using commercially available cloning systems (e.g., Lambda ZAP EXPRESS, Stratagene). Phage clones containing biomarker gene cDNAs may be identified by probing with a labeled biomarker cDNA or a fragment thereof. For example, in one embodiment, the biomarker cDNA or a portion thereof can be synthesized and used as a probe to retrieve overlapping and full length cDNAs corresponding to a biomarker gene. The biomarker gene itself may be isolated by screening genomic DNA libraries, bacterial artificial chromosome libraries (BACs), yeast artificial chromosome libraries (YACs), and the like, with biomarker DNA probes or primers.

The invention also provides recombinant DNA or RNA molecules containing a biomarker polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, e.g., Sambrook, et al. (1989) supra).

The invention further provides a host-vector system including a recombinant DNA molecule containing a biomarker polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as a Sf9 or HIGH-FIVE cell). Examples of suitable mammalian cells include various cancer cell lines, transfectable or transducible cancer cell lines, as well as a number of mammalian cells routinely used for the expression of recombinant proteins (e.g., COS, CHO, 293, 293T cells). More particularly, a polynucleotide including the coding sequence of a biomarker protein may be used to generate biomarker proteins or fragments thereof using any number of host-vector systems routinely used and widely known in the art.

A wide range of host-vector systems suitable for the expression of biomarker proteins or fragments thereof are available (see, e.g., Sambrook, et al. (1989) supra; Current Protocols in Molecular Biology (1995) supra). Exemplary vectors for mammalian expression include, but are not limited to, pcDNA 3.1 myc-His-tag (Invitrogen) and the retroviral vector pSRαtkneo (Muller, et al. (1991) MCB 11:1785). Using these expression vectors, biomarker protein may be expressed. Such host-vector systems can also be employed to study the functional properties of a biomarker protein and biomarker protein mutations.

Gene products or proteins encoded by the biomarker genes, or by fragments thereof, have a variety of uses. Such uses include, but are not limited to, generating antibodies and use in methods for identifying ligands and other agents and cellular constituents that bind to a biomarker gene product. Antibodies raised against a biomarker protein or fragment thereof may be useful in diagnostic and prognostic assays, and imaging methodologies in the management of human cancers characterized by expression of the biomarker protein, including but not limited to cancers of the kidney lung, colon, prostate, brain, bladder, pancreas, ovaries, lung, and breast. Antibodies can be raised by the conventional methods disclosed herein or any other suitable method. Such antibodies can be expressed intracellularly and used in methods of treating patients with such cancers. Various immunological assays useful for the detection of biomarker proteins are contemplated, including but not limited to FACS analysis, various types of radioimmunoassays, enzyme-linked immunosorbent assays (ELISA), enzyme-linked immunofluorescent assays (ELIFA), immunocytochemical methods, and the like. Such antibodies can be labeled and used as immunological imaging reagents capable of detecting biomarker expressing cells (e.g., in radioscintigraphic imaging methods). Biomarker proteins can also be particularly useful in generating cancer vaccines.

The present invention also features biomarker gene products, i.e., proteins and fragments thereof. The biomarker proteins of the invention include those specifically identified herein, as well as allelic variants, conservative substitution variants and homologs that can be isolated/generated and characterized without undue experimentation following the methods outlined herein. Fusion proteins that combine parts of different biomarker proteins or fragments thereof, as well as fusion proteins of a biomarker protein and a heterologous polypeptide are also included. Such biomarker proteins will be collectively referred to as biomarker proteins, marker proteins, or biomarker gene products. Specific embodiments of the invention embrace a biomarker protein listed in Table 1 and/or Table 2 or a fragment thereof. As used herein, a fragment or a protein of a biomarker protein is intended to mean a 6 to 50 amino acid residue portion of a biomarker protein. In some embodiments, a fragment is 6 amino acid residues, 15 amino acid residues, 30 amino acid residues, or 50 amino acid residues.

In general, naturally occurring allelic variants of a biomarker protein of the invention will share a high degree of structural identity and homology (e.g., 90% or more identity). Typically, allelic variants of the biomarker protein will contain conservative amino acid substitutions within a biomarker protein sequences described herein or will contain a substitution of an amino acid from a corresponding position in a biomarker protein homologue. One class of biomarker protein allelic variants will be proteins that share a high degree of homology with at least a small region of a particular biomarker protein amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of proteins such as polypeptides having amino acid insertions, deletions and substitutions. Variants can be made using methods known in the art such as site-directed mutagenesis, alanine scanning, and PCR mutagenesis. Site-directed mutagenesis (Carter, et al. (1986) *Nucl. Acids Res.* 13:4331; Zoller, et al. (1987) *Nucl. Acids Res.* 10:6487), cassette mutagenesis (Wells, et al. (1985) *Gene* 34:315), restriction selection mutagenesis (Wells, et al. (1986) *Philos. Trans. R. Soc. London Ser. A* 317:415) or other known techniques can be performed on the cloned DNA to produce the variant DNA. Scanning ammo acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia (1976) *J. Mol. Biol.* 150:1). If alanine substitution does not yield adequate amounts of variant, an isosteric amino acid can be used.

As defined herein, biomarker protein variants have the distinguishing attribute of having at least one epitope in common with a biomarker protein having an amino acid sequence disclosed in Table 1 or Table 2, such that an antibody that specifically binds to a biomarker protein variant will also specifically bind to the biomarker protein of Table 1 or Table 2, respectively. A polypeptide ceases to be a variant when it no longer contains an epitope capable of being recognized by an antibody that specifically binds to a biomarker protein. Those skilled in the art understand that antibodies that recognize proteins bind to epitopes of varying size, and a grouping of the order of about six amino acids, contiguous or not, is regarded as a typical number of amino acids in a minimal epitope. See e.g., Hebbes, et al. (1989) *Mol. Immunol.* 26(9):865-73; Schwartz, et al. (1985) *J. Immunol.* 135(4):2598-608. As there are approximately 20 amino acids that can be included at a given position within the minimal 6 amino acid epitope, an approximation of the odds of such an epitope occurring by chance are about $20^6$ or about 1 in 64 million. Another specific class of biomarker protein variants shares 90% or more identity with an amino acid sequence listed in Table 1 or Table 2.

Biomarker proteins of the invention have a number of different specific uses. As the biomarker proteins of the invention are associated with transformed cells, cells undergoing Contact Normalization, and malignant and metastatic cancers, these proteins can be used in methods assessing the status of biomarker gene products in normal versus cancerous tissues, and elucidating the malignant phenotype. Exemplary assays can use agents, e.g., antibodies, targeting or binding a biomarker protein disclosed herein. Alternatively, biomarker proteins can be used to screen for factors that interact with said biomarker proteins.

The term "status" in the context of the present invention is used in its art accepted meaning and refers to the condition or state of a gene or its products. As specifically described herein, the status of a biomarker can be evaluated by a number of parameters known in the art. Typically an alteration in the status of a biomarker includes a change in the location of biomarker expressing cells and/or an increase or decrease in biomarker mRNA and/or protein expression.

Biomarker proteins can be embodied in many forms, preferably in isolated form. As used herein, a protein is said to be "isolated" when physical, mechanical or chemical methods are employed to remove the biomarker protein from cellular constituents that are normally associated with the protein. A skilled artisan can readily employ standard purification methods to obtain an isolated biomarker protein. A purified biomarker protein molecule will be substantially free of other proteins or molecules that impair the binding of biomarker to antibody or other ligand. The nature and degree of isolation and purification will depend on the intended use.

Biomarker proteins can be generated using standard peptide synthesis technology or using chemical cleavage methods well-known in the art based on the amino acid sequences of the biomarker proteins disclosed herein. Alternatively, recombinant methods can be used to generate polynucleotides that encode a biomarker protein. In this regard, the biomarker-encoding polynucleotides described herein provide means for generating full-length and defined fragments of biomarker proteins.

The biomarker proteins of the present invention can also be modified in a way to form a chimeric molecule containing a biomarker protein fused to another, heterologous polypeptide or amino acid sequence. In one embodiment, such a chimeric molecule is a fusion of the biomarker protein with a polyhistidine epitope tag, which provides an epitope to which immobilized nickel can selectively bind. The epitope tag is generally placed at the amino- or carboxyl-terminus of the biomarker protein. In an alternative embodiment, the chimeric molecule can include a fusion of the biomarker protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a biomarker protein in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428, 130.

Antibodies are also embraced by this invention. The term "antibody" is used in the broadest sense and specifically covers single anti-biomarker protein monoclonal antibodies (including agonist, antagonist and neutralizing antibodies) and anti-biomarker protein antibody compositions with polyepitopic specificity. The term "monoclonal antibody" (mAb) as used herein refers to an antibody obtained from a population of substantially homogeneous antibodies. Desirably, antibodies of the invention will specifically bind to a biomarker protein and will not bind (or will bind weakly) to non-biomarker proteins and polypeptides. Anti-biomarker antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

Antibodies of the invention are particularly useful as binding agents in cancer diagnostic and prognostic assays, and imaging methodologies. Intracellularly expressed antibodies (e.g., single chain antibodies) may be therapeutically useful in treating cancers in which the expression of the biomarker protein is involved, such as, for example advanced and metastatic cancers. Biomarker-specific antibodies may also be used therapeutically by, for example, modulating or inhibiting the biological activity of a biomarker protein or targeting and destroying cancer cells expressing a biomarker protein or biomarker protein binding partner. In this regard, particular embodiments embrace antagonistic antibodies for use in inhibiting the activity of biomarker proteins herein.

The invention also provides various immunological assays useful for the binding to, detection and quantification of biomarker proteins. Such methods and assays generally include one or more biomarker-specific antibodies capable of recognizing and binding a biomarker protein, as appropriate, and can be performed within various immunological assay formats well-known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing biomarker proteins are also provided by the invention, including but not limited to radioscintigraphic imaging methods using labeled biomarker protein-specific antibodies. Such assays may be clinically useful in the detection, monitoring, and prognosis of cancers such as prostate, breast, pancreas, colon and ovarian cancers. Antibodies may also be used in methods for purifying biomarker proteins and for isolating biomarker protein homologues and related molecules.

Various methods for the preparation of antibodies are well-known in the art. For example, antibodies may be prepared by immunizing a suitable mammalian host using a biomarker protein, peptide, or fragment, in isolated or immunoconjugated form (Harlow & Lane, eds. (1988) Antibodies: A Laboratory Manual, CSH Press). In addition, fusion proteins can also be used, such as a biomarker protein GST-fusion. In other embodiments, a biomarker peptide may be synthesized and used as an immunogen.

In addition, naked DNA immunization techniques known in the art can be used (with or without purified biomarker protein or biomarker protein expressing cells) to generate an immune response to the encoded immunogen (for review, see Donnelly, et al. (1997) Ann. Rev. Immunol. 15:617-648).

Methods for preparing a protein or peptide for use as an immunogen and for preparing immunogenic conjugates of a protein with a carrier such as BSA, KLH, or other carrier proteins are well-known in the art. In some circumstances, direct conjugation using, for example, carbodimide reagents can be used; in other instances linking reagents such as those supplied by Pierce Chemical Co., Rockford, Ill., may be effective. Administration of a biomarker protein immunogen is conducted generally by injection over a suitable time period and with use of a suitable adjuvant, as is generally understood in the art. During the immunization schedule, titers of antibodies can be taken to determine adequacy of antibody formation.

Monoclonal antibodies are preferred and may be produced by various means well-known in the art. For example, immortalized cell lines that secrete a desired monoclonal antibody can be prepared using the standard hybridoma technology of Kohler and Milstein or modifications that immortalize producing B cells, as is generally known. The immortalized cell lines secreting the desired antibodies are screened by immunoassay in which the antigen is the biomarker protein or protein fragment. When the appropriate immortalized cell culture secreting the desired antibody is identified, the cells may be expanded and antibodies produced either from in vitro cultures or from ascites fluid.

Antibodies or fragments can also be produced by recombinant means. Regions that bind specifically to the desired regions of the biomarker protein can also be produced in the context of chimeric or CDR grafted antibodies of multiple species origin. Humanized or human antibodies can also be produced and are preferred for use in therapeutic contexts. Methods for humanizing murine and other non-human antibodies by substituting one or more of the non-human antibody CDRs for corresponding human antibody sequences are well-known (see, for example, Jones, et al. (1986) Nature 321:522-525; Riechmann, et al. (1988) Nature 332:323-327; Verhoeyen, et al. (1988) Science 239:1534-1536). Methods for producing fully human monoclonal antibodies include phage display and transgenic methods (for review, see Vaughan, et al. (1998) Nature Biotechnology 16:535-539).

Fully human monoclonal antibodies can be generated using cloning technologies employing large human Ig gene combinatorial libraries (i.e., phage display). Fully human monoclonal antibodies can also be produced using transgenic mice engineered to contain human immunoglobulin gene loci as described in WO 98/24893. This method avoids the in vitro manipulation required with phage display technology and efficiently produces high affinity authentic human antibodies.

Reactivity or binding of antibodies with a biomarker protein can be established by a number of well-known means, including western blot, immunoprecipitation, ELISA, and FACS analyses using, as appropriate, biomarker proteins, peptides, or cell extracts.

An antibody or fragment thereof of the invention can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the antibody can be selected in accordance with the intended use. For example, for therapeutic use, the second molecule can be a toxin or therapeutic agent.

Further, bi-specific antibodies specific for two or more epitopes may be generated using methods generally known in the art. Homodimeric antibodies may also be generated by cross-linking techniques known in the art (e.g., Wolff, et al. (1993) Cancer Res. 53:2560-2565).

Polynucleotides encoding biomarkers of the present invention can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding a biomarker of the invention can be used to clone genomic DNA encoding the biomarker in accordance with established techniques and the genomic sequences used to generate transgenic animals that contain cells that express DNA encoding the biomarker. Methods for generating transgenic animals, particularly animals such as mice or rats, have become conventional in the art and are described, for example, in U.S. Pat. Nos. 4,736,866 and 4,870,009. Typically, particular cells would be targeted for transgene incorporation with tissue-specific enhancers. Transgenic animals that include a copy of a transgene encoding the biomarker introduced into the germ line of the animal at an embryonic stage can be used to examine the effect of increased expression of DNA encoding the biomarker. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, biomarkers of the invention can be used to construct a "knock out" animal that has a defective or altered gene encoding the biomarker as a result of homologous recombination between the endogenous gene encoding the biomarker and altered genomic DNA encoding the biomarker introduced into an embryonic cell of the animal. For example, cDNA encoding a biomarker can be used to clone genomic DNA encoding the biomarker in accordance with established techniques. A portion of the genomic DNA encoding the biomarker can be deleted or replaced with another gene, such as a gene encoding a selectable biomarker that can be used to monitor integration. Typically, several kilobases of unaltered flanking DNA (both at the 5' and 3' ends) are included in the vector (see e.g., Thomas & Capecchi (1987) Cell 51:503) for a description of homologous recombination vectors). The vector is introduced into an embryonic stem cell line (e.g., by electroporation) and cells in which the introduced DNA has homologously recombined with the endogenous DNA are selected (see e.g., Li, et al. (1992) Cell 69:915). The selected cells are then injected into a blastocyst of an animal (e.g., a mouse or rat) to form aggregation chimeras (see e.g., Bradley, in Robertson, ed. (1987) Teratocarcinomas and Embryonic Stem Cells: A Practical Approach, (IRL, Oxford), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the biomarker protein.

The present invention also features methods for detecting biomarker genes and biomarker gene products, as well as methods for identifying a cell that aberrantly expresses the biomarker. The analysis disclosed herein indicates that biomarkers of the present invention are aberrantly expressed in transformed cells or cells affected by Contact Normalization. In this context, the status of biomarker gene products can provide information useful for predicting a variety of factors including susceptibility to advanced stage disease, rate of progression, and/or tumor aggressiveness. The status of biomarker gene and gene products in patient samples can be analyzed by a variety protocols that are well-known in the art including immunohistochemical analysis, the variety of northern blotting techniques including in situ hybridization, RT-PCR analysis (for example on laser capture micro-dissected samples), western blot analysis and tissue array analysis using agents disclosed herein that bind biomarker genes and gene products.

More particularly, the invention provides assays for diagnosing and prognosing cancer by detecting the presence or quantity of biomarker gene polynucleotides in a biological sample, such as serum, bone, biopsy samples and other tissues, urine, semen, cell preparations, and the like. Biological samples can be obtained from any mammalian source including human, mouse, dog, cat, or horse subjects. Detectable biomarker polynucleotides include, for example, mRNA, and recombinant DNA or RNA molecules containing a biomarker polynucleotide. A number of methods for amplifying and/or detecting the presence or quantity of polynucleotides are well-known in the art and may be employed in the practice of this aspect of the invention.

In one embodiment, a method for detecting a biomarker gene mRNA in a biological sample includes obtaining a sample, producing cDNA from the sample by reverse transcription using at least one primer that binds the biomarker polynucleotide; amplifying the cDNA so produced using biomarker oligonucleotides as sense and antisense primers to amplifying cDNAs therein; and detecting the presence of the amplified cDNA. Such assays can be qualitative or quantitative. Any number of appropriate sense and antisense probe combinations may be designed from the polynucleotide sequences disclosed in Table 1 or Table 2.

The invention also provides assays for diagnosing and prognosing cancer by detecting the presence or quantity of a biomarker protein in a biological sample such as serum, bone, biopsy sample or other tissues, urine, cell preparations, and the like. Methods for detecting a biomarker protein are also well-known and include, for example, immunoprecipitation, immunohistochemical analysis, western blot analysis, molecular binding assays, ELISA, ELIFA and the like. For example, in one embodiment, a method of detecting the presence of a biomarker protein in a biological sample includes obtaining a sample from a subject, contacting the sample with an agent that binds the biomarker protein, e.g., a biomarker-specific antibody, and then determining the binding of the agent to the biomarker protein in the sample, wherein the presence of binding is indicative of the presence of the biomarker protein in the sample and hence cancer. Such assays can be qualitative or quantitative.

Methods for identifying a cell that aberrantly expresses a biomarker protein are also provided. A cell that aberrantly expresses a biomarker is intended to mean a cell exhibiting an elevated or reduced level of expression of a biomarker as compared to a control. As disclosed herein, such a comparison can be between transformed and nontransformed cells, or transformed cells and transformed cells affected by Contact Normalization. Biomarkers and their expression in transformed cells are provided in Table 3.

In one embodiment, an assay for identifying a cell that aberrantly expresses a biomarker gene includes detecting the presence or quantity of biomarker mRNA in the cell. Methods for the detection of particular mRNAs in cells are well-known and include, for example, hybridization assays using complementary DNA probes (such as in situ hybridization using labeled riboprobes, northern blot and related techniques) and various nucleic acid amplification assays (such as RT-PCR using complementary primers specific for the biomarker, and other amplification type detection methods, such as, for example, branched DNA, SISBA, TMA and the like). Alternatively, an assay for identifying a cell that aberrantly expresses a biomarker gene includes detecting the presence or quantity of a biomarker protein in the cell or secreted by the cell. Various methods for the detection of proteins are well-known in the art and may be employed for the detection of biomarker proteins and biomarker expressing cells.

The expression profile of a biomarker makes it a potential diagnostic biomarker for local and/or metastasized disease. In particular, the status of a biomarker may provide information useful for predicting susceptibility to particular disease stages, progression, and/or tumor aggressiveness. The invention provides methods and assays for determining biomarker status and diagnosing cancers that express the biomarker, such as cancers of the prostate, bladder, bladder, kidney, ovaries, breast, pancreas, colon and lung. Biomarker status in patient samples can be analyzed by a number of means well-known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the gene and gene products can be found, for example in standard laboratory manuals, e.g., as disclosed herein.

Biomarker expression analysis may also be useful as a tool for identifying and evaluating agents that modulate biomarker gene expression. For example, biomarkers with an elevated level of expression in a cancer cell can be used in the identification of a molecule or biological agent that could inhibit biomarker expression or over-expression in cancer cells. Such an agent may be identified by using a screen that quantifies biomarker expression by RT-PCR, nucleic acid hybridization or antibody binding to the gene product.

The biomarker protein sequences disclosed herein also allow the skilled artisan to identify proteins, antibodies, small molecules and other agents that interact with the biomarkers and pathways activated by the biomarkers via any one of a variety of art accepted protocols.

In this regard, the present invention also embraces a method of identifying a chemotherapeutic agent by contacting a biomarker gene or gene product of the invention with a test compound and determining whether the test compound modulates (increases or decreases) the expression of the biomarker gene or expression or activity of the biomarker gene product.

For example, one can identify agents that interact with biomarker protein sequences by screening one or more libraries of compounds. Such libraries can be natural, semi-synthetic or synthetic compounds of various class, e.g., peptide, proteins, carbohydrates, lectins, antibodies, small organic molecules, and the like. By way of illustration, peptide libraries and screening methods that can be used to identify molecules that interact with biomarker protein sequences are disclosed in U.S. Pat. Nos. 5,723,286 and 5,733,731.

Small organic molecules that interact with biomarker proteins can be identified through related embodiments of such screening assays. For example, small molecules can be identified that interfere with protein function, including molecules that interfere with the ability of the biomarker to mediate tumorigenesis. Typical methods are discussed for example in U.S. Pat. No. 5,928,868 and include methods forming hybrid ligands in which at least one ligand is a small molecule.

Agents that inhibit the expression or activity of biomarker genes or gene products which are elevated in transformed cells are useful as chemotherapeutic agents in the prevention and treatment of cancer, in particular malignant and metastatic cancer. Agents that enhance the expression or activity of tumor suppressor gene or gene products which are decreased in transformed cells are also useful as chemotherapeutic agents. In addition, molecules identified in such screen can be used as diagnostic reagents.

The identification of the biomarkers disclosed herein opens a number of therapeutic approaches to the treatment of such cancers including malignant and metastatic cancers. Accordingly, therapeutic approaches aimed at modulating the expression or activity of the biomarker proteins are expected to be useful for patients with cancer or patients harboring cancer cells affected by Contact Normalization. These therapeutic approaches aimed at modulating the expression or activity of a biomarker protein generally fall into two classes. One class includes various methods for modulating the binding or association of the biomarker protein with its binding partner or with other proteins. Another class includes a variety of methods for modulating the transcription of the biomarker gene or translation of biomarker mRNA.

A number of typical antibody strategies are known in the art for targeting both extracellular and intracellular molecules (e.g., complement and ADCC-mediated killing or the use of intrabodies). Because the biomarkers of the present invention are expressed by cancer cells and not by corresponding normal cells, systemic administration of biomarker-immunoreactive compositions would be expected to exhibit excellent sensitivity without toxic, non-specific and/or non-target effects caused by binding of the immunotherapeutic molecule to non-target organs and tissues. Antibodies can be useful to treat cancers systemically, either as conjugates with a toxin or therapeutic agent, or as naked antibodies capable of inhibiting cell proliferation or function (i.e., antagonistic antibodies).

Antibodies can be introduced into a patient such that the antibody binds to the cognate biomarker protein and modulates or perturbs a function such as an interaction with a binding partner and consequently mediates the growth inhibition and/or destruction of the cells and the tumor and/or inhibits the growth of the cells or the tumor.

Cancer immunotherapy using antibodies may follow the teachings generated from various approaches that have been successfully employed in the treatment of other types of cancer, including but not limited to colon cancer (Arlen, et al. (1998) *Crit. Rev. Immunol.* 18:133-138), multiple myeloma (Ozaki, et al. (1997) *Blood* 90:3179-3186; Tsunenari, et al. (1997) *Blood* 90:2437-2444), gastric cancer (Kasprzyk, et al. (1992) *Cancer Res.* 52:2771-2776), leukemia (Zhong, et al. (1996) *Leuk. Res.* 20:581-589), colorectal cancer (Moun, et al. (1994) *Cancer Res.* 54:6160-6166; Velders, et al. (1995) *Cancer Res.* 55:4398-4403), and breast cancer (Shepard, et al. (1991) *J. Clin. Immunol.* 11:117-127). Some therapeutic approaches involve conjugation of naked antibody to a toxin, such as the conjugation of $^{131}$I to anti-CD20 antibodies (e.g., RITUXAN, IDEC Pharmaceuticals Corp.), while others involve co-administration of antibodies and other therapeutic agents, such as HERCEPTIN (trastuzumab) with paclitaxel (Genentech, Inc Therapeutic methods of the invention contemplate the administration of single mAbs as well as combinations, or cocktails, of different mAbs. Such mAb cocktails may have certain advantages inasmuch as they contain mAbs that target different epitopes, different biomarkers, exploit different effector mechanisms or combine directly cytotoxic mAbs with mAbs that rely on immune effector functionality. Such mAbs in combination may exhibit synergistic therapeutic effects. In addition, the administration of mAbs may be combined with other therapeutic agents, including but not limited to various chemotherapeutic agents, androgen-blockers, and immune modulators (e.g., IL-2, GM-CSF). The mAbs may be administered in their "naked" or unconjugated form, or may have therapeutic agents conjugated to them.

Antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the antibody preparation via an acceptable route of administration such as intravenous injection (IV), typically at a dose in the range of about 0.1 to about 10 mg/kg body weight. Doses in the range of 10-500 mg mAb per week may be effective and well tolerated.

Based on clinical experience with the HERCEPTIN mAb in the treatment of metastatic breast cancer, an initial loading dose of approximately 4 mg/kg patient body weight IV followed by weekly doses of about 2 mg/kg IV of the mAb preparation may represent an acceptable dosing regimen.

As indicated, another therapeutic approach includes the use of methods and compositions for modulating the transcription and/or translation of a biomarker gene. By way of illustration, a method of inhibiting the transcription of a biomarker gene involves contacting the biomarker gene or mRNA with an antisense polynucleotide or siRNA. In another approach, a biomarker-specific ribozyme may be used to cleave the biomarker message, thereby inhibiting translation. Such siRNA-, antisense- and ribozyme-based methods may also be directed to the regulatory regions of the biomarker gene, such as the start site, promoter and/or enhancer elements. Similarly, proteins capable of inhibiting a gene transcription factor may be used to inhibit biomarker mRNA transcription. The various polynucleotides and compositions useful in the aforementioned methods are described herein. The use of antisense and ribozyme molecules to inhibit transcription and translation is well-known in the art.

In vivo, the effect of a therapeutic composition may be evaluated in a suitable animal model. For example, xenogenic cancer models wherein human cancer explants or passaged xenograft tissues are introduced into immune compromised animals, such as nude or SCID mice, are appropriate in relation to cancer and have been described (Klein. et al. (1997) *Nature Medicine* 3:402-408). For example, WO 98/16628 describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like.

The therapeutic compositions used in the practice of the foregoing methods can be formulated into pharmaceutical compositions including a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Ed., A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection includes the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

For use in the diagnostic and therapeutic applications described herein, kits are also provided by the invention. Such kits may include a carrier means being compartmentalized to receive in close confinement one or more container means such as vials, tubes, and the like, each of the container means including one of the separate elements to be used in the method. For example, one of the container means may contain a probe that is or can be detectably labeled. Such probe may be an antibody or oligonucleotide specific for a biomarker protein or a biomarker gene or message, respectively. Where the kit utilizes nucleic acid hybridization to detect the target nucleic acid, the kit may also have containers containing nucleotide(s) for amplification of the target nucleic acid sequence and/or a container having a reporter-means, such as a biotin-binding protein, such as avidin or streptavidin, bound to a reporter molecule, such as an enzymatic, florescent, or radioisotope label.

The kit of the invention will typically include the container described above and one or more other containers including materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

The invention is described in greater detail by the following non-limiting examples.

Example 1

Materials and Methods

Cell culture. Nontransformed and Src transformed wild-type mouse embryonic fibroblasts (WT), homozygous null Cx43 knockout brain cells (Cx43Ko), and homozygous null Cas knockout cells (CasKo) are known in the art (Goldberg, et al. (2003) *J. Biol. Chem.* 278:46533-46540; Shen, et al. (2006) *Cancer Res.* 66:1543-1552; Alexander, et al. (2004) *Cancer Res.* 64:1347-1358; Patwardhan, et al. (2006) *J. Biol. Chem.* 281:20689-20697). cDNA encoding murine Pdpn was released from pCMV-Sports-pdpn (Open Biosystems #MMM1013-7513215) with EcoRI and XbaI and inserted into the complementary sites of pEF4 to create pEF4Pdpn. Cells were transfected with pEF4Pdpn, empty pEF4 vector, siRNA directed against mouse Pdpn, or control siRNA (Dharmacon, Chicago, Ill.) with LIPOFECTAMINE 2000 (Li, et al. (2008) *Cancer Sci.* 99:1326-1333; Shen, et al. (2007) *J. Biol. Chem.* 282:18914-18921). Cells transfected with pEF4 expression vectors were selected with zeocin. Clones were not taken from any cell lines, thus minimizing potential effects of clonal variation.

Layered Culture System. A Layered Culture System was used to allow separated populations of transformed and non-transformed cells to form intercellular junctions with each other as described (Alexander, et al. (2004) supra; Goldberg, et al. (2002) *J. Biol. Chem.* 277:36725-26730). Briefly, 10 thousand Src transformed cells were plated on porous membranes (Costar) containing 300 thousand nontransformed cells on the other side. Transformed cells and nontransformed cells were able to form intercellular junctions through the pores in the membrane; however, the membrane pore size (3 µm) is small enough to prevent cells (about 20 µm in diameter) from actually migrating to the other side of the membrane (Shen, et al. (2006) supra; Alexander, et al. (2004) supra; Goldberg, et al. (2002) supra). Transformed cells were also plated alone, directly above 300 thousand nontransformed cells, or 1 mm above 300 thousand nontransformed cells as controls. Nontransformed cells were also plated on these membranes as controls. Cells were harvested and analyzed 24 hours after plating.

Expression Microarrays. Gene expression in nontransformed, Src transformed, and contact normalized Cx43Ko cells was examined by microarray analysis with 430 2.0 Mouse Expression Array gene chips (Affymetrix) using conventional methods (Shen, et al. (2006) supra). These arrays contain approximately 45,000 probe sets which represent over 30,000 genes. Affected probe sets displayed a difference of at least 4-fold between transformed and control cells, or at least a 2-fold change with $p<0.05$ by t-test with $n=3$. Genes that were increased by Contact Normalization were also decreased by Src, but not affected by diffusible factors from nontransformed cells or contact with other transformed cells. Conversely, genes that were decreased by Contact Normalization were increased by Src, but not affected by diffusible factors from nontransformed cells or contact with other transformed cells. All comparisons were done with cells from parallel cultures to control for variability in reagents or experimental conditions. Expression analysis was performed with Vector Xpression software 4.0 (Invitrogen).

RT-PCR. RNA was purified with Tri-reagent (Sigma, St. Louis, Mo.). cDNA was synthesized from 1 µg of RNA by with PROTOSCRIPT First Strand cDNA Synthesis Kit (NEB, Ipswich, Mass.). PCR was performed with 1 µl of cDNA with forward and reverse primers specific for GAPDH (5'-TGC ATC CTG CAC CAC CAA CT-3', SEQ ID NO:1; and 5'-TGC CTG CTT CAC CAC CTT C-3', SEQ ID NO:2), hygromycin phosphotransferase (5'-CAT GGC GTG ATT TCA TAT GCG CGA-3', SEQ ID NO:3; and 5'-TCC AGA AGA AGA TGT TGG CGA CCT-3', SEQ ID NO:4), puromycin acetyltransferase (5'-ACC GAG CTG CAA GAA CTC TTC CTC-3', SEQ ID NO:5; and 5'-AGG AGG CCT TCC ATC TGT TGC T-3', SEQ ID NO:6), Pdpn (5'-ACC AAC ACA GAC GAC CAA GAC ACT-3', SEQ ID NO:7; and 5'-AAG CAT CCA CTG TGC CTT CAG TTC-3', SEQ ID NO:8), Fhl1 (5'-GAG AAG TTC GAC TGT CAC TAC TGC-3', SEQ ID NO:9; and 5'-CTG ATC CTG GTA AGT GAT TCC TCC-3', SEQ ID NO:10), 4930408O21Rik (5'-TGT TCT CAG AGC CCA GCA TCA CTT-3', SEQ ID NO:11; and 5'-ACA TCC TCT CAG CTG GTT CCT TCA-3', SEQ ID NO:12), 1700012B09Rik (5'-CTG TGA ACC GCA TAA GAG AAT CAA GGA GG-3', SEQ ID NO:13; and 5'-TGC CTC GAG TAG TAC TTG GCT TGT-3', SEQ ID NO:14), Tmem163 (5'-ATA GAG TCT GTC ATC ATG GGC TGG-3', SEQ ID NO:15; and 5'-ACA GGC TTC CTG TCA AGC AGA GA-3', SEQ ID NO:16), Loc677224 (5'-AAC ATC CCA GAG CCT TTG ACT CCT-3', SEQ ID NO:17; and 5'-CAA AGC TGC CAT AGC TCT ATT CGG-3', SEQ ID NO:18), 1810008K04Rik (5'-AAG CCA GGA CTC TCA CAT GCA ACT-3', SEQ ID NO:19; and 5'-AGC TTT GCA GAT GGA ACG GAA CAC-3', SEQ ID NO:20), and D4bwg0951e (5'-TGG ATG GCA TCT CAG TAG GGA GCT A-3', SEQ ID NO:21; and 5'-TTG CAC ACC AGT CCC ATG CAA A-3', SEQ ID NO:22). GAPDH was amplified at 95° C. for 5 minutes, 95° C. for 30 seconds, 55° C. for 30 seconds, and 72° C. for 30 seconds for 30 cycles, followed by 72° C. for 5 minutes. Hygromycin phosphotransferase was amplified at 95° C. for 5 minutes, 95° C. for 30 seconds, and 72° C. for 1 minute for 30 cycles, followed by 72° C. for 5 minutes. The other genes were amplified at 95° C. for 5 minutes, 95° C. for 30 seconds, 60° C. for 30 seconds, and 72° C. for 30 seconds for 30 cycles, followed by 72° C. for 5 minutes.

Western Blot Analysis. Western blot analysis was performed according to conventional methods (Shen, et al. (2006) supra). Protein (10 µg/lane) was resolved by SDS-PAGE, transferred to IMMOBILON-P membranes (Millipore), and incubated with antisera specific for Pdpn (Santa Cruz Biotechnology), Cas (Santa Cruz Biotechnology), active Src kinase (Cell Signaling Technology), v-Src (Upstate Biotechnology), or β-actin (Sigma). Primary antiserum was recognized by appropriate secondary antiserum conjugated to horseradish peroxidase and detected using Enhanced Chemiluminescence (Millipore). After blotting, membranes were stained with India ink to verify equal loading and transfer.

Immunofluorescence Microscopy. Cells (300,000) were cultured on 35-mm poly-D-lysine-coated glass-bottomed culture dishes (MatTek) for 24 hours. For some experiments, lectin from *Maackia amurensis* (Sigma) was conjugated to TEXAS RED (Anaspec) incubated with cells for 15 minutes at 37° C. Cells were fixed with 2% paraformaldehyde, permeabilized with 0.2% TRITON X-100 in PBS (phosphate-buffered saline) for 10 minutes, washed thrice with 0.1% TWEEN 20 in PBS followed by 1% bovine serum albumin (BSA) in PBS for 30 minutes, incubated with Pdpn antiserum (1:100) overnight at 4° C., washed, and then labeled with goat anti-syrian hamster IgG conjugated to ALEXA FLUOR 488 (Molecular Probes). Cells were visualized on ZEISS AXIO-VERT or PASCAL microscope systems (Li, et al. (2008) supra; Shen, et al. (2007) supra).

Cell Growth, Migration, and Toxicity Assays. Cell growth and migration were assayed according to established methods (Shen, et al. (2006) supra; Li, et al. (2008) supra). Briefly, anchored and nonanchored growth were measured by plating 20,000 cells per well on standard 12-well cluster plates (Falcon) or ultra low attachment 24-well cluster plates (Corning), respectively, and counting cells at defined times by Coulter counter. To examine membrane cell migration, 200,000 cells were plated on cell culture inserts with a 8µ pore size (Transwell-Clear, Costar) in 6-well cluster plates and grown for 24 hours. Cells were then separately released from the top of the membrane, bottom of the membrane, and well beneath the membrane and counted. Migration and colonization was quantified as the percentage of cells that moved to the bottom of the membrane or well beneath the membrane, respectively. Cell migration was also examined by a wound healing assay and quantified as the number of cells that entered a 1.8 mm$^2$ or 0.9 mm$^2$ area of the wound during 24 hours. Cells were stained with 0.2% trypan blue and counted with a hemocytometer to evaluate cytotoxicity.

Affinity Precipitation. Cells were lysed in lysis buffer (20 mM Tris-Cl pH 7.4, 150 mM NaCl, 0.5% TRITON X-100, 1 mM PMSF) on ice for 30 minutes, clarified by centrifugation, diluted to 1 mg/ml in PBS supplemented with 1 mM PMSF and 10 mM MgCl$_2$, and incubated with lectin from *M. amurensis* (Sigma) conjugated to agarose beads or empty beads as controls (Thermo Scientific), on ice for 3 hours. Beads were then washed 4 times with PBS, and eluted in of SDS-PAGE sample buffer at 95° C. for 5 minutes. Eluted protein was examined along with total cell lysates by western blot analysis.

Example 2

Screening Assay for Genes Associated with Contact Normalization

Tumor cells must overcome contact normalization by adjacent nontransformed cells in their microenvironment to become malignant or metastatic (Rubin (2007) *Adv. Cancer Res.* 98:117-147). Using a layered culture system, identify genes involved in this process (Shen, et al. (2006) *Cancer Res.* 66:1543-1552; Alexander, et al. (2004) *Cancer Res.* 64:1347-1358) were identified. As shown in FIG. 1, Src transformed cells were incubated on a porous membrane directly over nontransformed cells. The transformed cells and nontransformed cells were able to form intercellular junctions through the pores in the membrane while being retained as separate populations. Thus, although intercellular junctions formed between the transformed and nontransformed cells, the layers were retained as distinct populations that were separately harvested. As controls, transformed cells were also incubated alone, or 1 mm over nontransformed cells to enable communication by diffusible factors but not direct contact. As has been previously reported, cellular material is not transferred between harvested cell layers (Shen, et al. (2006) supra; Alexander, et al. (2004) supra; Goldberg, et al. (2002) *J. Biol. Chem.* 277:36725-36730). This was verified by the retention of the Src kinase and mRNA encoding puromycin acetyltransferase in the transformed cells, and mRNA encoding hygromycin phosphotransferase in nontransformed cells.

Using AFFYMETRIX microarrays, mice genes involved in Contact Normalization were identified. About 45,000 probe sets were examined, representing over 39,000 transcripts. The expression of genes represented by 10928 probe sets, or up to about 25% of the transcriptome, was affected 2-fold or more by Src. The expression of genes represented by up to 5560 probe sets was higher in Src transformed cells than nontransformed cells, while the expression of genes represented by up to 5368 probe sets was lower. However, only 39 genes were found to be significantly affected by Contact Normalization of Src transformed cells (Table 3). The mRNA levels of several of these genes, including Pdpn, Tmem163, Fhl1, and 5 ESTs were verified by RT-PCR. The expression of these genes was clearly affected by Src and reversed by contact with nontransformed cells.

TABLE 3

| Gene Symbol | Nucleotide Accession No. | Fold Change Src[a] | CN[b] |
|---|---|---|---|
| *Genes Increased by Src and Decreased During Contact Normalization* | | | |
| 1700012B09Rik[c] | NM_029306 | 115 | −3.4 |
| Pdpn[c] | NM_010329 | 93 | −4.7 |
| Tmem163[c] | NM_028135 | 58 | −5.5 |
| Smoc2 | NM_022315 | 47 | −6.6 |
| Pstpip2 | NM_013831 | 41 | −4.5 |
| Mal | NM_010762 | 30 | −5.6 |
| Lepr | NM_146146 | 28 | −4.7 |
| Elavl2 | NM_207685 | 26 | −9.9 |
| Igsf11 | NM_170599 | 26 | −5.0 |
| Mafb | NM_010658 | 14 | −6.7 |
| LOC677224[c] | XR_034093. | 13 | −3.5 |
| 4930408O21Rik[c] | NM_001040136 | 8.8 | −4.8 |

TABLE 3-continued

| Gene Symbol | Nucleotide Accession No. | Fold Change Src[a] | CN[b] |
|---|---|---|---|
| Elmod1 | NM_177769 | 8.3 | −5.0 |
| Atp13a4 | NM_172613 | 7.8 | −4.7 |
| Kdr | NM_010612 | 6.6 | −3.7 |
| C9 | NM_013485 | 5.4 | −4.9 |
| *Genes Decreased by Src and Increased During Contact Normalization* | | | |
| Fgf7 | NM_008008 | −130 | 46 |
| D10Bwg1379e | NM_001033258 | −95 | 13 |
| Sox11 | NM_009234 | −93 | 16 |
| Ccl20 | NM_016960 | −91 | 12 |
| Vcam1[d] | NM_011693 | −78* | 22* |
| | | −56* | 16* |
| | | −55* | 12* |
| Sema3e | NM_011348 | −71 | 8.3 |
| Sdpr[d] | NM_138741 | −47 | 13* |
| | | −39 | 11* |
| Epha4 | NM_007936 | −44 | 8.3 |
| Ntn1 | NM_008744 | −42 | 17 |
| Cabc1 | NM_023341 | −32 | 5.0 |
| Spry1 | NM_011896 | −26 | 4.5 |
| Loxl1 | NM_010729 | −25 | 9.9 |
| 1810008K04Rik[c] | NM_001081050 | −19 | 9.0 |
| Pdgfrb | NM_008809 | −18 | 3.9 |
| D4Bwg0951e[c] | NM_026821 | −17 | 4.2 |
| Fhl1[c,d] | NM_001077361 | −16 | 11 |
| Gpr126 | NM_001002268 | −16* | 5.7* |
| | | −13* | 5.7* |
| Egfr | NM_207655 | −16 | 5.2 |
| Itih2 | NM_010582 | −12 | 7.3 |
| Epb4.1l3 | NM_013813 | −12 | 5.6 |
| Il1rl1 | NM_001025602 | −9.7 | 8.3 |
| Wnt5a | NM_009524 | −9.1 | 4.6 |
| Tmem56 | NM_178936 | −8.2 | 4.4 |

[a]Expression in Src transformed cells divided by expression in nontransformed cells.
[b]Expression in transformed cells divided by expression in transformed cells undergoing Contact Normalization.
[c]Effects confirmed by RT-PCR.
[d]Genes previously shown to be induced by Contact Normalization.
*Represent results with different probe sets.

As shown in Table 3, the expression of 23 genes was suppressed by Src and increased by contact normalization. Some of these genes encode proteins that mediate events including growth factor signaling (Fgf7, Epha4, Spry1, Pdgfrb, Gpr126, Egfr, Wnt5a, and Il1rl1) and transcription (Sox11 and Fhl1). Many of these genes have been implicated in the regulation of tumor cell growth and migration. For example, recent experiments indicate that Epb4.1l3 (erythrocyte protein band 4.1-like 3) (Cavanna, et al. (2007) *J. Cell Sci.* 120:606-616) and Itih2 (inter-alpha-trypsin inhibitor heavy chain) (Werbowetski-Ogilvie, et al. (2006) *Cancer Res.* 66:1464-1472) can suppress tumor cell invasion and metastasis. Induction of three of these genes, Vcam1, Sdpr, and Fhl1 is associated with contact normalization (Alexander, et al. (2004) supra). Interestingly, these genes are candidate biomarkers that are suppressed in malignant tumor cells (Li, et al. (2008) *Cancer Sci.* 99:1326-1333). For example, Src utilizes Cas to suppress Fhl1 expression in order to promote tumor cell migration (Shen, et al. (2006) supra).

The expression of 16 genes was increased by Src and suppressed by contact normalization. These genes are of great interest since they may be required for malignant growth and metastasis. These genes encode proteins that mediate events including cation (Smoc2, Atp13a4) and glutamate (Tmem163) transport, neuronal development (Mal), energy homeostasis (Lepr), mRNA transcription (Mafb) and stabilization (Elavl2), cell adhesion (Igsf11), growth factor signaling (Kdr), and immunological activity (C9). Some of these gene products may act as biomarkers and targets for chemotherapy. For example, inhibitors have been generated to target kinase insert domain receptor (Kdr) in order to prevent VEGF signaling and suppress angiogenesis required for malignant tumor growth (Schenone, et al. (2007) *Curr. Med. Chem.* 14:2495-2516). Immunological reagents have also been targeted to immunoglobulin superfamily 11 (IGSF11) (Watanabe, et al. (2005) *Cancer Sci.* 96:498-506) and podoplanin (Pdpn) (Kato, et al. (2008) *Cancer Sci.* 99:54-61) in order to prevent tumor cell invasion and metastasis.

Since the gap junction protein Cx43 can affect transformed cell migration (Xu, et al. (2006) *Development* 133:3629-3639; Shao, et al. (2005) *Cancer Res.* 65:2705-2711), the effects of Src on Pdpn expression were analyzed in Cx43Ko (knock out) and wild-type cells. While more Pdpn was found in wild-type cells than Cx43Ko cells, western blot analysis revealed that Src augmented Pdpn protein expression in both cell types. These findings were confirmed by immunofluorescence microscopy.

These data indicate that Pdpn acts downstream of Src and Cas along the pathway leading to nonanchored tumor cell growth and migration. This study presents an example of how genes that are induced by Src and suppressed by Contact Normalization can be utilized as biomarkers and promising targets for chemotherapy. These genes also find application in assessing the role of the proteins encoded thereby in malignant growth potential.

Example 3

Src Utilizes Cas to Induce Pdpn Expression

Pdpn expression was notably affected by Src and Contact Normalization. This was intriguing since Pdpn can promote tumor cell migration leading to malignant and metastatic growth (Wicki, et al. (2007) *Br. J. Cancer* 96:1-5; Kato, et al. (2008) supra; Nakazawa, et al. (2008) *Blood* 112(5):1730-9). It has been found that Src utilizes Cas to suppress Fhl1 expression in order to promote nonanchored cell growth and migration of Src transformed cells (Shen, et al. (2006) supra). Therefore, the effects of Src on Pdpn expression were examined in cells with and without Cas. This analysis indicated that more Pdpn was found in Src transformed cells CasKo cells transfected with Cas than control transfectants. These data indicate that Src utilizes Cas to augment Pdpn expression and promote tumor cell migration.

The effects of Pdpn on the motility of Src transformed cells were examined by transfection with siRNA. This analysis indicated that Pdpn protein expression was decreased in Src transfected cells transfected with siRNA directed against Pdpn. Wound healing assays showed that this decrease in Pdpn expression reduced the migration of Src transformed cells by over 60%. These data indicate that Src induced Pdpn expression to promote cell migration.

The effects of Pdpn on the motility of nontransformed cells were also examined by transfection with cDNA. Western blot analysis demonstrated that nontransformed cells, transfected with cDNA encoding Pdpn, expressed Pdpn protein levels comparable to Src transformed cells. Immunofluorescent microscopy found Pdpn localized to the plasma membrane where it may act as a signaling receptor. Pdpn expression did not significantly affect the growth or anchorage dependence of nontransformed cells. However, Pdpn expression did augment the ability of nontransformed cells to migrate by over 5 fold, achieving levels comparable to Src transformed cells. Thus, Pdpn did not require transforming Src activity to promote cell migration. Nonetheless, since Pdpn did not augment nonanchored growth, it was not sufficient to increase colonization of nontransformed cells.

Figure 2A:
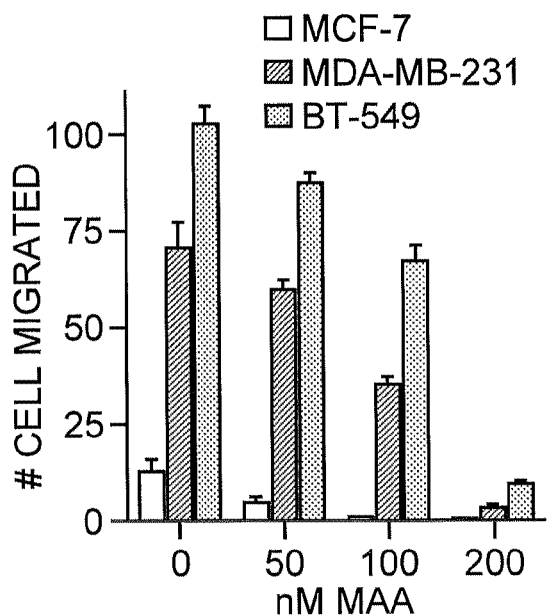
FIG. 2 shows the effect of lectins in a wound healing migration assay (FIG. 2A) and toxicity assay (FIG. 2B). Migration assays were performed on confluent monolayers of cells treated with varying concentrations of *Maackia amurensis* lectin (MAA) as indicated. Data are shown as the number of cells that migrated into a 300×300 micron area along the center of the wound in 24 hours (mean±SEM, n=7). MAA toxicity was evaluated by Trypan blue staining of cells from wound healing assays. Data are shown as the percent of live cells from equivalent samples of each well (mean+SEM, n=4).
Figure 2B:
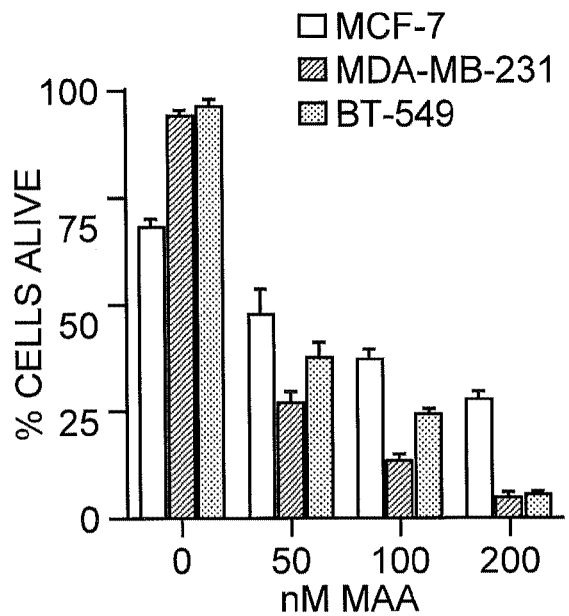

In addition to Src transformed mouse cells, Pdpn expression levels were also examined along with the migration of human mammary carcinoma cells. This analysis indicated that levels of Pdpn expression correlated well with the migration of MCF7, MDA-MB-231, BT-549 cells shown in FIG. 2. These data are consistent with Pdpn augmenting the migration of epithelial tumor cells.

Example 4

Plant Lectins Bind Pdpn

Pdpn is a membrane-bound extracellular glycoprotein that associates with endogenous lectins to promote cell motility that is required for tumor cell invasion and metastasis (Wicki et al. (2007) supra; Scholl, et al. (1999) *J. Cell Sci.* 112:4601-4613; Martin-Villar, et al. (2006) *J. Cell Sci.* 119:4541-4553). Thus, blocking Pdpn activity should also block malignant cell growth and metastasis. Specific plant lectins can bind to oligosaccharides contained on Pdpn. For example, seeds from the legume tree *M. amurensis* contain lectins (MAA) with an affinity for O-linked carbohydrate chains containing sialic acid (Imberty, et al. (2000) *J. Biol. Chem.* 275:17541-17548; Van Damme, et al. (1997) *Glycoconj. J.* 14:449-456). This analysis indicated that MAA associated with Pdpn on the membrane of Src transformed cells. In addition, this compound associated with Pdpn in cell lysates during affinity precipitation experiments.

Along with binding to Pdpn, lectin from *M. amurensis* inhibited the migration of Src transformed cells. This lectin suppressed tumor cell migration by about 30% at 50 nM and over 60% at 100 nM. Results from trypan blue staining indicated that this compound affected cell migration before inducing cytotoxic effects. In addition, these concentrations appeared to preferentially inhibit the migration of Src transformed cells before affecting the migration of nontransformed cells. Statistical analysis indicates that interaction between v-Src expression and MAA exposure accounted for 12% of the variation between samples (p<0.005 by two-way ANOVA).

The lectin jacalin, derived from the jackfruit tree *Artocarpus integrifolia*, was used as a control in these studies because it preferentially binds to glycoconjugates containing galactosyl (β1,3) N-acetylgalactosamine (Lehmann, et al. (2006) *Cell Mol. Life. Sci.* 63:1331-1354). In contrast to MAA, jacalin does not reduce cell migration at nontoxic concentrations and appeared to augment cell migration at concentrations of up to 400 nM. Thus, suppression of tumor cell migration appeared to be lectin-specific and consistent with binding to extracellular moieties presented by Pdpn.

The targeting of MAA to Pdpn was examined by comparing its effects on nontransformed cells transfected with Pdpn or control transfectants. This analysis indicated that MAA reduced the migration of Pdpn transfected cells in a dose-dependent fashion. This effect was much less significant in control transfectants. In particular, 50 nM MAA decreased the migration of Pdpn transfectants by over 40%, but increased the migration of control transfectants by about 35%. Statistical analysis indicated that interaction between Pdpn expression and MAA exposure accounted for 26% of the variation between samples (p<0.0001 by two-way ANOVA). In addition to inhibiting cell migration, MAA appeared preferentially toxic to Pdpn expressing cells. 200 nM MAA decreased trypan blue exclusion of Pdpn transfectants by over 70%, but control transfectants by about 20%.

Indeed, the interaction between Pdpn expression and MAA exposure accounted for 18% of the variation between samples ($p<0.0001$ by two-way ANOVA).

The effects of MAA on human mammary carcinoma cells also correlated well with Pdpn expression. MAA was more effective on BT-549 and MDA-MB-231 cells, which expressed high levels of Pdpn, than MCF-7 cells, which expressed lower levels. The interaction between cell type and MAA exposure accounted for 18% of the variation of migration between samples (FIG. 2A) and 10% of the variation of toxicity between samples (FIG. 2B) ($p<0.0001$ by two-way ANOVA).

It is contemplated that like MAA, there are other natural lectins that may bind to Pdpn and prevent tumor cell growth. For example, as shown in Table 4, the *M. amurensis* lectins are composed of two types of lectin molecules (MAH and MAL), which display slightly different binding preferences. Data indicate that this mixture can specifically suppress anchorage-independence and motility of Src transformed cells at nM concentrations. Analysis of MAH and MAL separately can determine if either of these compounds is more effective at preventing malignant cell growth than the mixture found in nature.

TABLE 4

| Organism | Species or Cell Type | Lectin | Binding Specificity |
|---|---|---|---|
| Virus | Sendai virus | HN | NeuAcα2,3Galβ1,3GalNac/4GlcNAc |
| | Human parainfluenza virus type 1 | HN | NeuAcα2,3Galβ1,4GlcNac |
| Bacteria | *Streptococcus mitis* | SABP | Neu5Acα2,3Galβ1,3GalNac |
| | *Mycoplasma pneumoniae* | HA-A | Neu5Acα2,3Galβ1,4GlcNAcβ1,3 |
| Fungi | *Polyporus squamosus* | PSA | Neu5Acα2,6Galβ1,4Glc/GlcNAc |
| | *Psathyrella vetutina* | PVS | Neu5Acα2,6Galβ1,4GlcNAc |
| | *Macrophomina phaseolina* | MPL | Neu5Acα2,3Galβ1,4GlcNAc |
| Plants | *Maackia amurensis* | MAL | Neu5Acα2,3Galβ1,4GlcNAc |
| | | MAH | Neu5Acα2,3Galβ1,3[Neu5Acα2,6]GalNAc |
| | *Trichosanthes japonica* | TJA | Neu5Acα2,6Galβ1,4GlcNAc |
| | *Viscum album* | ML-1 | Neu5Acα2,6Galβ1,4GlcNAc |
| | *Artocarpus intergrifolia* | jacalin | Gal and Man > Neu5Ac |
| Insects | *Allomyrina dichotoma* | Allo A-II | Neu5Acα2,6Galβ1,4GlcNAc |
| Animals | blood macrophages | IL-1α Siglec-1 | Neu5Acα2,3Galβ1,4GlcNAc Neu5Acα2,3Gal |

As shown in Table 4, sialic acid binding lectins can be derived from virus, bacterial, fungal, plant, insect, and animal sources. For example, analysis herein indicates that jacalin, which preferentially associates with glycoconjugates containing galactosyl (β1,3) N-acetylgalactosamine, may actually augment tumor cell migration. In contrast, MAH or MAL, which preferentially associate with O-glycosidically linked oligosaccharides having galactosyl (β1,4) N-acetylglucosamine structures with (α2,3) linked sialic acid, can prevent nonanchored tumor cell growth and migration. Taken together, this analysis indicates that specific lectins can associate with Pdpn and suppress nonanchored cell growth and migration required for tumor cell invasion and progression, thereby demonstrating efficacy of targeting the gene or gene products disclosed herein that are affected during Contact Normalization.

In addition, it is expected that lectins can be analyzed for similar binding specificities, such as MPL from *M. phaseolina* and TJA from *T. japonica*. These compounds can be obtained from a variety of sources including Sigma-Aldrich, Calbiochem, and Vector Laboratories.

Fluorescence microscopy can be used to determine if specific lectins colocalize with Pdpn. Pdpn is visualized by detection with antiserum specific for Pdpn. HILYTE FLUOR TR (AnaSpec) is directly conjugated to amine groups on the lectins. HILYTE FLUOR TR displays a strong fluorescence signal similar to TEXAS Red. Confocal fluorescence microscopy is used to determine if Pdpn and lectin molecules colocalize on transformed cells.

Immunoprecipitation is also used to determine if Pdpn and lectins associate with each other. Pdpn can be immunoprecipitated from cell lysates, and coprecipitated lectin can be visualized with a PHOSPHORIMAGER. Antisera targeted to different proteins are used in control experiments to validate the specificity of these immunoprecipitation experiments. Precipitation of target proteins can be verified by Western blotting.

Ligand-based western blot analysis is used to determine if specific lectins bind to Pdpn. Whole cell lysates of immunoprecipitated protein can be resolved by PAGE and transferred to IMMOBOLIN membranes. Membranes are then incubated with labeled lectin and antiserum against Pdpn. Colocalization is determined as described above.

To determine if lectins that bind to Pdpn can suppress nonanchored growth and migration of Src transformed cells, Src transformed cells and nontransformed cells are treated with various concentrations of specific lectins that bind to Pdpn, as well other lectins with different binding affinities (see, e.g., Table 4). Mouse embryonic fibroblasts and other established cell lines, including LA25 cells, can be used for these experiments. Cells are plated on standard tissue culture dishes or ultra low attachment dishes to measure anchored growth and nonanchored growth, respectively. Cells are also be plated on porous (e.g., COSTAR TRANSWELL) membranes to measure migration. Wound healing assays and video microscopy are also be used to assess cell migration rates. These experiments are be performed on parallel cultures to obtain accurate quantitative comparisons between cell types. The effects of several concentrations of specific lectins on the anchored growth, nonanchored growth, and migration of Src transformed and nontransformed cells are quantitated. It is expected that specific lectins will inhibit the malignant growth potential of tumor cells at concentration that will not inhibit the "normal" growth of nontransformed cells. This is demonstrated by showing that specific lectins significantly inhibit nonanchored growth and migration of transformed cells, without significantly interfering with the anchored growth of parental nontransformed control cells.

Example 5

Model Systems for Analyzing Biomarkers and Chemotherapeutic Targets

Cell systems of use in identifying biomarkers and chemotherapeutic targets to specifically detect and neutralize malignant and metastatic cancer cells that are not controlled by Contact Normalization are listed in Table 5. Using such systems it has been found that Src induces the expression of Pdpn and promotes anchorage independence and motility required for tumor cell invasion metastasis. It has also been demonstrated that some plant lectins can bind to podoplanin and inhibit nonanchored tumor cell growth and motility at nontoxic concentrations. Therefore, natural products and compounds derived from natural products can be used in the prevention of malignant progression without harming other cells of the body.

TABLE 5

| Cells | Src | Cas | Pdpn | Anch. Independ. | Migration |
|---|---|---|---|---|---|
| CasKO (homozygous null Cas knockout cells) | | | | | |
| CasKOHP | − | − | − | − | − |
| CasKOHP-Pdpn | (−) | (−) | (+) | (+) | (+) |
| CasKOHP-Ef4 | (−) | (−) | (−) | (−) | (−) |
| CasWt | − | + | − | − | − |
| CasKOSrc | + | − | − | − | − |
| CasWtSrc | + | + | + | + | + |
| CasWtSrc-siCas | (+) | (−) | (−) | (−) | (−) |
| CasWtSrc-siPdpn | (+) | (+) | (−) | (−) | (−) |
| CasWtSrc-siCntl | (+) | (+) | (+) | (+) | (+) |

TABLE 5-continued

| Cells | Src | Cas | Pdpn | Anch. Independ. | Migration |
|---|---|---|---|---|---|
| MEF (mouse embryonic fibroblasts) | | | | | |
| Mef | − | + | − | − | − |
| Mef-Pdpn | (−) | (+) | (+) | (+) | (+) |
| Mef-Ef4 | (−) | (+) | (−) | (−) | (−) |
| MefSrc | + | + | + | + | + |
| MefSrc-siCas | (+) | (−) | (−) | (−) | (−) |
| MefSrc-siPdpn | (+) | (+) | (−) | (−) | (−) |
| MefSrc-siCntl | (+) | (+) | (+) | (+) | (+) |
| LA25 (temperature sensitive Src transformants) | | | | | |
| LA25-34° C. | + | + | + | + | + |
| LA25-siCas-34° C. | + | − | (−) | (−) | (−) |
| LA25-siPdpn-34° C. | (+) | (+) | (−) | (−) | (−) |
| LA25-siCntl-34° C. | + | + | (+) | (+) | (+) |
| LA25-39° C. | − | + | − | − | − |
| LA25Ef4-39° C. | (−) | (+) | (−) | (−) | (−) |
| LA25Pdpn-39° C. | (−) | (+) | (+) | (+) | (+) |

Anticipated results are shown in parentheses.

What is claimed is:

1. A method of diagnosing or prognosing cancer comprising obtaining a biological sample from a subject suspected of having cancer, measuring the expression of Transmembrane protein 163 (Tmem163) and Podoplanin (Pdpn) biomarker gene or gene products in the biological sample, and comparing the expression of the Tmem163 and Pdpn biomarker gene or gene products in the biological sample to the expression of the Tmem163 and Pdpn biomarker gene or gene products in a control sample to determine whether there is an increase in the expression of Tmem163 and Pdpn, wherein increased expression of the Tmem163 and Pdpn biomarker gene or gene products in the biological sample compared to expression in the control sample is indicative of cancer.

2. The method of claim 1, further comprising measuring the expression of one or more of the biomarker gene or gene products selected from the group of RIKEN cDNA 1700012B09 gene (1700012B09Rik), SPARC related modular calcium binding 2 (Smoc2), Proline-serine-threonine phosphatase-interacting protein 2 (Pstpip2), Myelin and lymphocyte protein (Mal), Leptin receptor (Lepr), Embryonic lethal abnormal vision-like 2 (Elavl2), Immunoglobulin superfamily member 11 (Igsf11), v-maf protein B (Mafb), Similar to RIKEN cDNA 2810457106 (LOC677224), RIKEN cDNA 4930408021 gene (4930408021Rik), ELMO domain containing 1 (Elmod1), ATPase type 13A4 (Atp13a4), Kinase insert domain protein receptor (Kdr), Complement component 9 (C9), Fibroblast growth factor 7 (Fgf7), DNA segment Chr 10 Brigham & Women's Genetics 1379 expressed (D10Bwg1379e), SRY-box containing gene 11 (Sox11), Chemokine (C-C motif) ligand 20 (Ccl20), Semaphorin 3E (Sema3e), EPH receptor A4 (Epha4), Netrin 1 (Ntn1), Chaperone ABC1 activity of bc1 complex homolog (Cabc1), Sprouty homolog 1 (Spry1), Lysyl oxidase-like 1 (Loxl1), Par-3 partitioning defective 3 homolog B (Pard3b), Platelet-derived growth factor receptor beta polypeptide (Pdgfrb), DNA segment Chr 4 Brigham & Women's Genetics 0951 expressed (D4Bwg0951e), G protein-coupled receptor 126 (Gpr126), Epidermal growth factor receptor (Egfr), Inter-alpha trypsin inhibitor heavy chain 2 (Itih2), Erythrocyte membrane protein band 4.1-like 3 (Epb4l3), Interleukin 1 receptor-like 1 (Il1rl1), Wingless-related MMTV integration site 5A (Wnt5a), Transmembrane protein 56 (Tmem56), Vascular cell adhesion molecule 1 (Vcam1), Serum deprivation response (Sdpr), and Four and a half LIM domains 1 (Fhl1).

3. A kit for detecting cancer cells comprising
(a) an agent that binds a Transmembrane protein 163 (Tmem163) biomarker gene or gene product; and
(b) an agent that binds a Podoplanin (Pdpn) biomarker gene or gene product.

4. The kit of claim 3, wherein said agent is an antibody.

5. The kit of claim 3, further comprising an agent that binds a biomarker gene or gene product selected from the group of RIKEN cDNA 1700012B09 gene (1700012B09Rik), SPARC related modular calcium binding 2 (Smoc2), Proline-serine-threonine phosphatase-interacting protein 2 (Pstpip2), Myelin and lymphocyte protein (Mal), Leptin receptor (Lepr), Embryonic lethal abnormal vision-like 2 (Elavl2), Immunoglobulin superfamily member 11 (Igsf11), v-maf protein B (Mafb), Similar to RIKEN cDNA 2810457106 (LOC677224), RIKEN cDNA 4930408021 gene (4930408021Rik), ELMO domain containing 1 (Elmod1), ATPase type 13A4 (Atp13a4), Kinase insert domain protein receptor (Kdr), Complement component 9 (C9), Fibroblast growth factor 7 (Fgf7), DNA segment Chr 10 Brigham & Women's Genetics 1379 expressed (D10Bwg1379e), SRY-box containing gene 11 (Sox11), Chemokine (C-C motif) ligand 20 (Ccl20), Semaphorin 3E (Sema3e), EPH receptor A4 (Epha4), Netrin 1 (Ntn1), Chaperone ABC1 activity of bc1complex homolog (Cabc1), Sprouty homolog 1 (Spry1), Lysyl oxidase-like 1 (Loxl1), Par-3 partitioning defective 3 homolog B (Pard3b), Platelet-derived growth factor receptor beta polypeptide (Pdgfrb), DNA segment Chr 4 Brigham & Women's Genetics 0951 expressed (D4Bwg0951e), G protein-coupled receptor 126 (Gpr126), Epidermal growth factor receptor (Egfr), Inter-alpha trypsin inhibitor heavy chain 2 (Itih2), Erythrocyte membrane protein band 4.1-like 3 (Epb4l3), Interleukin 1 receptor-like 1 (Il1rl1), Wingless-related MMTV integration site 5A (Wnt5a), Transmembrane protein 56 (Tmem56), Vascular cell adhesion molecule 1 (Vcam1), Serum deprivation response (Sdpr), and Four and a half LIM domains 1 (Fhl1).

6. A method of identifying an agent capable of inhibiting tumor cell migration comprising contacting a cell expressing Transmembrane Protein 163 (TMEM163) with a test compound and determining whether the test compound interferes with the cell migration promoting activity of TMEM163.

7. A method for inhibiting tumor cell growth in vitro comprising contacting a tumor cell expressing Transmembrane Protein 163 (TMEM163) in vitro with an agent that inhibits the expression of TMEM163 or the cell migration promoting activity of TMEM163.

8. The method of claim 7, wherein the agent is an anti-TMEM163 antagonistic antibody.

9. The method of claim 7, wherein the agent is a siRNA molecule targeted to TMEM163.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tgcatcctgc accaccaact                                          20

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
tgcctgcttc accaccttc                                           19

<210> SEQ ID NO 3
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 3
catggcgtga tttcatatgc gcga                                     24

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
tccagaagaa gatgttggcg acct                                     24

```
<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 5
accgagctgc aagaactctt cctc                                            24

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
aggaggcctt ccatctgttg ct                                              22

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7
accaacacag acgaccaaga cact                                            24

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 8
aagcatccac tgtgccttca gttc                                            24

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
gagaagttcg actgtcacta ctgc                                            24

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
ctgatcctgg taagtgattc ctcc                                            24

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 11
```

-continued tgttctcaga gcccagcatc actt                                    24

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
acatcctctc agctggttcc ttca                                    24

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 13
ctgtgaaccg cataagagaa tcaaggagg                               29

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
tgcctcgagt agtacttggc ttgt                                    24

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
atagagtctg tcatcatggg ctgg                                    24

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
acaggcttcc tgtcaagcag aga                                     23

<210> SEQ ID NO 17
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 17
aacatcccag agcctttgac tcct                                    24

<210> SEQ ID NO 18
<211> LENGTH: 24
<212> TYPE: DNA
<213> ORGANISM: Artificial sequence

```
<220> FEATURE:
<223> OTHER INFORMATION: Synthetic oligonucleotide

<400> SEQUENCE: 18
caaagctgcc atagctctat tcgg                                          24

<210> SEQ ID NO 19
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 19
aagccaggac tctcacatgc aact                                          24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
agctttgcag atggaacgga acac                                          24

<210> SEQ ID NO 21
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 21
tggatggcat ctcagtaggg agcta                                         25

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
ttgcacacca gtcccatgca aa                                            22
```